United States Patent
Martin et al.

(10) Patent No.: US 7,186,977 B2
(45) Date of Patent: Mar. 6, 2007

(54) METHOD FOR NON-DESTRUCTIVE TRENCH DEPTH MEASUREMENT USING ELECTRON BEAM SOURCE AND X-RAY DETECTION

(75) Inventors: Yves C. Martin, Ossining, NY (US); Anthony Santiago, Wappingers Falls, NY (US); Theodore G. van Kessel, Millbrook, NY (US)

(73) Assignee: International Business Machines Corporation, Armonk, NY (US)

(*) Notice: Subject to any disclaimer, the term of this patent is extended or adjusted under 35 U.S.C. 154(b) by 231 days.

(21) Appl. No.: 11/035,932

(22) Filed: Jan. 14, 2005

(65) Prior Publication Data
US 2006/0157649 A1    Jul. 20, 2006

(51) Int. Cl.
*H01J 37/256* (2006.01)
*G01N 23/223* (2006.01)

(52) U.S. Cl. .................. 250/310; 250/306; 250/307; 250/492.2

(58) Field of Classification Search ............... None
See application file for complete search history.

(56) References Cited

U.S. PATENT DOCUMENTS 6,388,756 B1 * 5/2002 Ho et al. .................. 356/626
6,834,117 B1 * 12/2004 Rao et al. ................. 382/149

* cited by examiner

*Primary Examiner*—Nikita Wells
(74) *Attorney, Agent, or Firm*—Casey P. August; McGinn IP Law Group PLLC

(57) ABSTRACT

A method (and system) for non-destructive measurement of a depth of a feature in a structure, includes using a scanning electron microscope (SEM) image to navigate to find the feature in an X-ray image, using an electron beam to produce a fluorescent emission in the feature, and using an X-ray count made at a position of the feature in the X-ray image, to determine a depth of the feature.

33 Claims, 4 Drawing Sheets

100

Silicon Xray Image

SEM Secondary Electron image

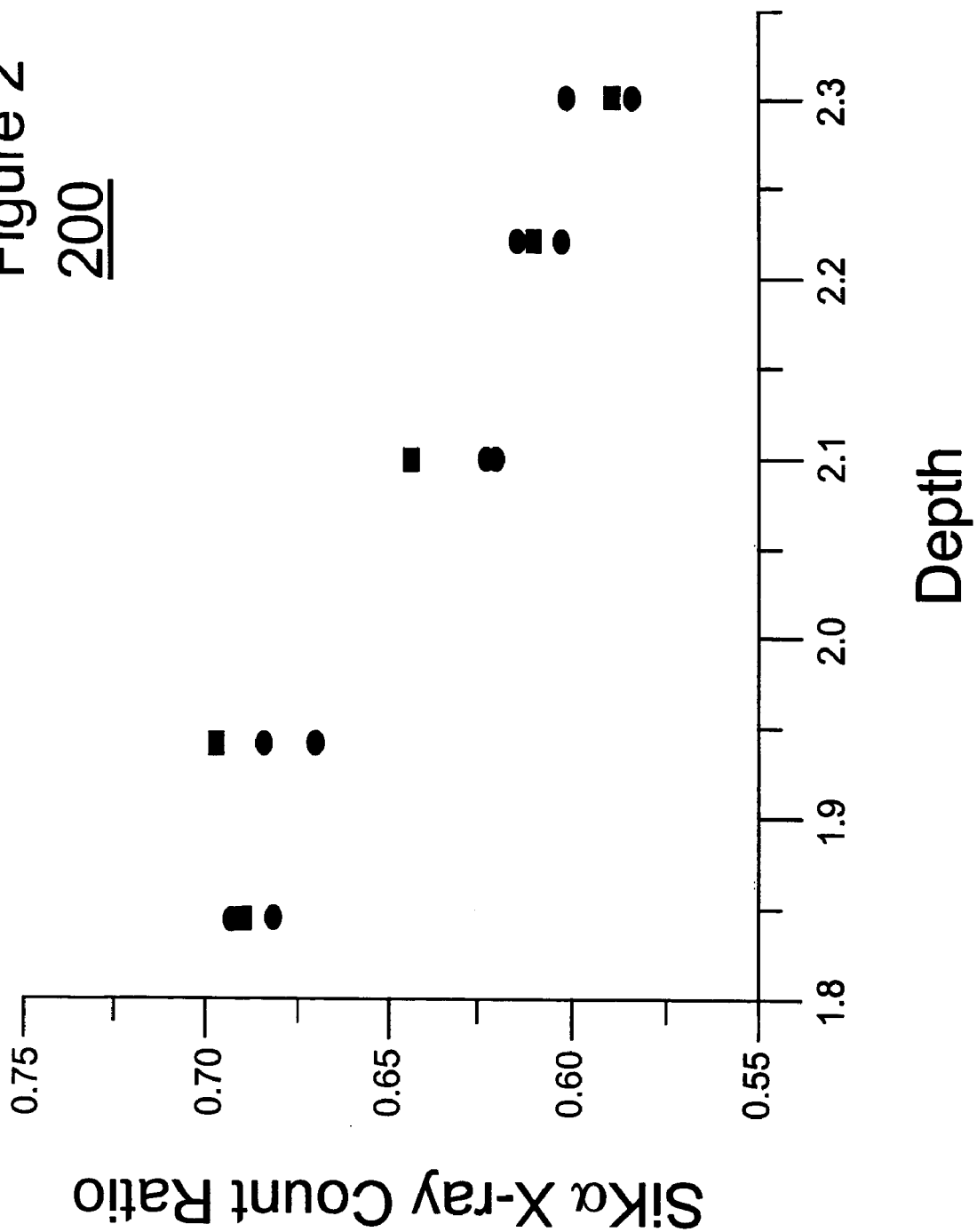

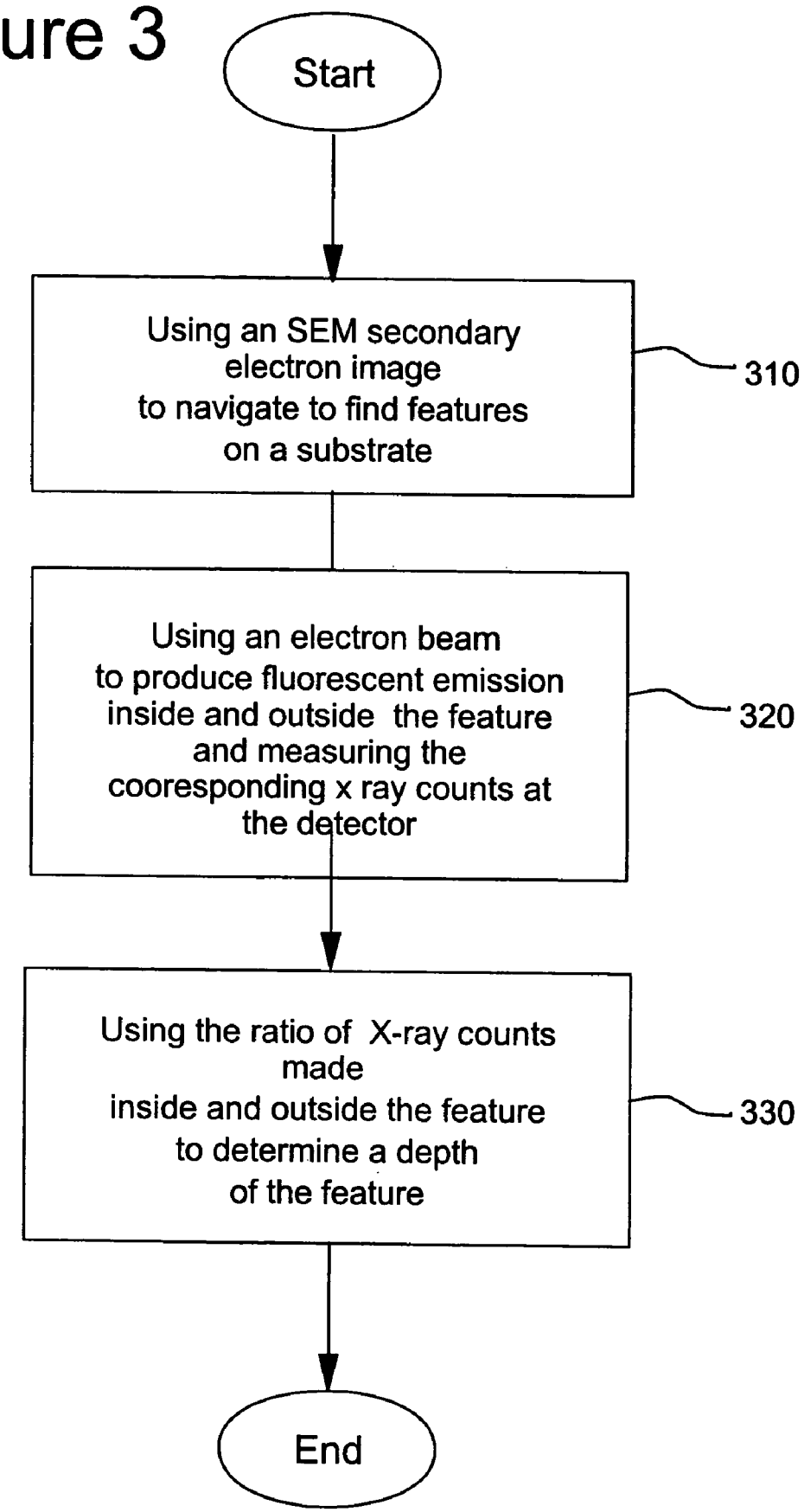

US 7,186,977 B2

METHOD FOR NON-DESTRUCTIVE TRENCH DEPTH MEASUREMENT USING ELECTRON BEAM SOURCE AND X-RAY DETECTION

BACKGROUND OF THE INVENTION

1. Field of the Invention

The present invention generally relates to the non-destructive measurement of high aspect trenches in semiconductor materials, and more particularly to a non-destructive trench depth measurement method and apparatus.

2. Description of the Related Art

High aspect ratio holes or trenches formed in silicon (or other semiconductor material) typically must be measured for various reasons relating to the proper operation of the devices being made and the control of the manufacturing process. These trenches are typically on the order of microns deep. In the context of the present disclosure, the trenches are typically of a depth ranging from 0.25 to 300 microns. In addition, the trenches are usually of high aspect (depth/width) and in at least one dimension have a width parameter that is small (e.g., a micron or fraction thereof), thereby making optical or atomic force microscope measurement (AFM) difficult or impossible. As discussed below, the present invention can certainly measure trenches outside the above parameters, but this is the area where the greatest advantage is to be found.

Thus, as a practical example, the depth parameter of high aspect ratio trench structures characteristic of dynamic random access memory (DRAM) and embedded DRAM (EDRAM) memory devices are difficult or impossible to measure using conventional non-destructive techniques including top-down scanning electron microscope (SEM) and atomic force microscopy (AFM) and optical microscopy due to narrow width (0.25 micron or less) and large depth (8 microns or so).

To monitor the performance of the processes that create these trench structures, it is necessary to employ costly destructive methods such as cleavage SEM in which the wafer (or a part thereof) is actually destroyed, thereby decreasing yield and raising costs.

Thus, prior to the present invention, there has been no technique which solves the above-mentioned and other problems, by enabling the non-destructive depth measurement of trench structures using a combination of scanning electron microscopy and energy dispersive X-ray spectroscopy.

Additionally, existing methods suffer from other difficulties. For example, atomic force microscopes (AFM) employ tapered tips which cannot physically reach the bottom of high aspect ratio trenches. Even in instances where nanotube tips are employed, the bending of the tip and sidewall stiction prevent accurate measurement of extremely high aspect structures. Further, optical microscopy cannot penetrate light deep into opaque structures with openings smaller than about 0.5 microns, and even then with very limited results. SEM measurement is similarly constrained in that there is no clear line of sight means of escape for back-scattered or secondary electrons at the bottom of the trench to reach the detector, thereby making imaging of this region difficult, if not impossible.

SUMMARY OF THE INVENTION

In view of the foregoing and other exemplary problems, drawbacks, and disadvantages of the conventional methods and structures, an exemplary feature of the present invention is to provide a method and structure in which non-destructive depth measurement of trench structures is enabled using a combination of scanning electron microscopy and energy dispersive X-ray spectroscopy.

In a first exemplary aspect of the present invention, a method of non-destructive measurement of a depth of a feature in a structure, includes navigating and locating the feature using a scanning electron microscope (SEM) image, producing fluorescent emissions in the feature using the electron beam from the SEM, producing fluorescent emissions outside the feature using the electron beam from the SEM, counting, using an X-ray detector and a counting apparatus, the fluorescent emissions located such that emissions outside the feature travel through less structure than those inside the feature, and determining a depth of the feature based on a count of the fluorescent emissions made at inside and outside positions of the feature.

In a second exemplary aspect of the present invention, an apparatus for non-destructive measurement of a depth of a feature in a structure, includes a scanning electron microscope (SEM) for producing an image for navigating to find the feature in an X-ray image; and a unit for using an X-ray count made at a position of the feature in the X-ray image, to determine a depth of the feature.

In a third exemplary aspect of the present invention, a system for non-destructive measurement of a depth of a feature in a structure, includes a scanning electron microscope (SEM) for scanning an electron beam across a surface of a substrate containing a feature, and an X-ray detector for detecting X rays produced when the electron beam strikes the surface of the substrate, and producing an X-ray image, wherein electrons from the electron beam impact the surface of the substrate and feature regions, thereby causing X rays to be produced adjacent a point of electron impact, the SEM forming an SEM image.

In a fourth exemplary aspect of the present invention, a method of measuring a depth of a trench in a material, includes scanning a surface to form a secondary electron emission (SE) image and simultaneously forming an X-ray image with an X-ray system, the X-ray image having fewer counts than the secondary electron image, and using the SE image to determine a location of the trench in the material and a location of a surface of the material.

In a fifth exemplary aspect of the present invention, a method of measuring a depth of a trench in a material, includes traversing a scanning beam across a surface having a trench, said scanning beam interacting with the sample to cause a detectable particle emission, and counting the detectable particle emission, to judge the depth of the trench.

In a sixth exemplary aspect of the present invention, a method, includes traversing a sample with a scanning beam of one of photons and particles, resulting in collision and emission of one of photon and particulate energy, and detecting the emission, attenuated by a material of the sample, to measure a dimension of a feature in the sample.

In a seventh exemplary aspect of the present invention, a method (and system) for non destructive measurement of a depth of a feature in a structure, includes using a scanning electron microscope (SEM) image to navigate to find the feature in an X-ray image, using an electron beam to produce a fluorescent emission in the feature, and using a count of the x ray emissions made at a position of the feature in the X-ray image and adjacent areas, to determine a depth of the feature.

With the unique and unobvious aspects of the present invention, the inventive structure takes advantage of the attenuation of X rays traveling through material. The present invention preferably employs an electron beam ("e-beam") from a scanning electron microscope to impact and generate X rays at the base region of a trench. Then, these X rays are detected at an angle such that they must travel through an amount of material that is proportional to the depth at which they are generated. By measuring this attenuation, the depth of the trench can be estimated.

Thus, the invention can reliably, easily and non-destructively measure a depth of trench structures using a combination of scanning electron microscopy and energy dispersive X-ray spectroscopy.

Another advantage of the invention is that there is in principle no practical limit to the depth of trenches measured by the inventive method. Trenches on the order of hundreds of microns can be measured with due consideration to beam current, energy and detection.

BRIEF DESCRIPTION OF THE DRAWINGS

The foregoing and other exemplary purposes, aspects and advantages will be better understood from the following detailed description of an exemplary embodiment of the invention with reference to the drawings, in which.

FIG. 2 illustrates a graph showing the dependence of X-ray counts on trench depth; and FIG. 3 illustrates a method 300 of performing non-destructive trench depth measuring using an electron beam source and an X-ray detection according to the present invention.

DETAILED DESCRIPTION OF EXEMPLARY EMBODIMENTS OF THE INVENTION

Figure 1A:
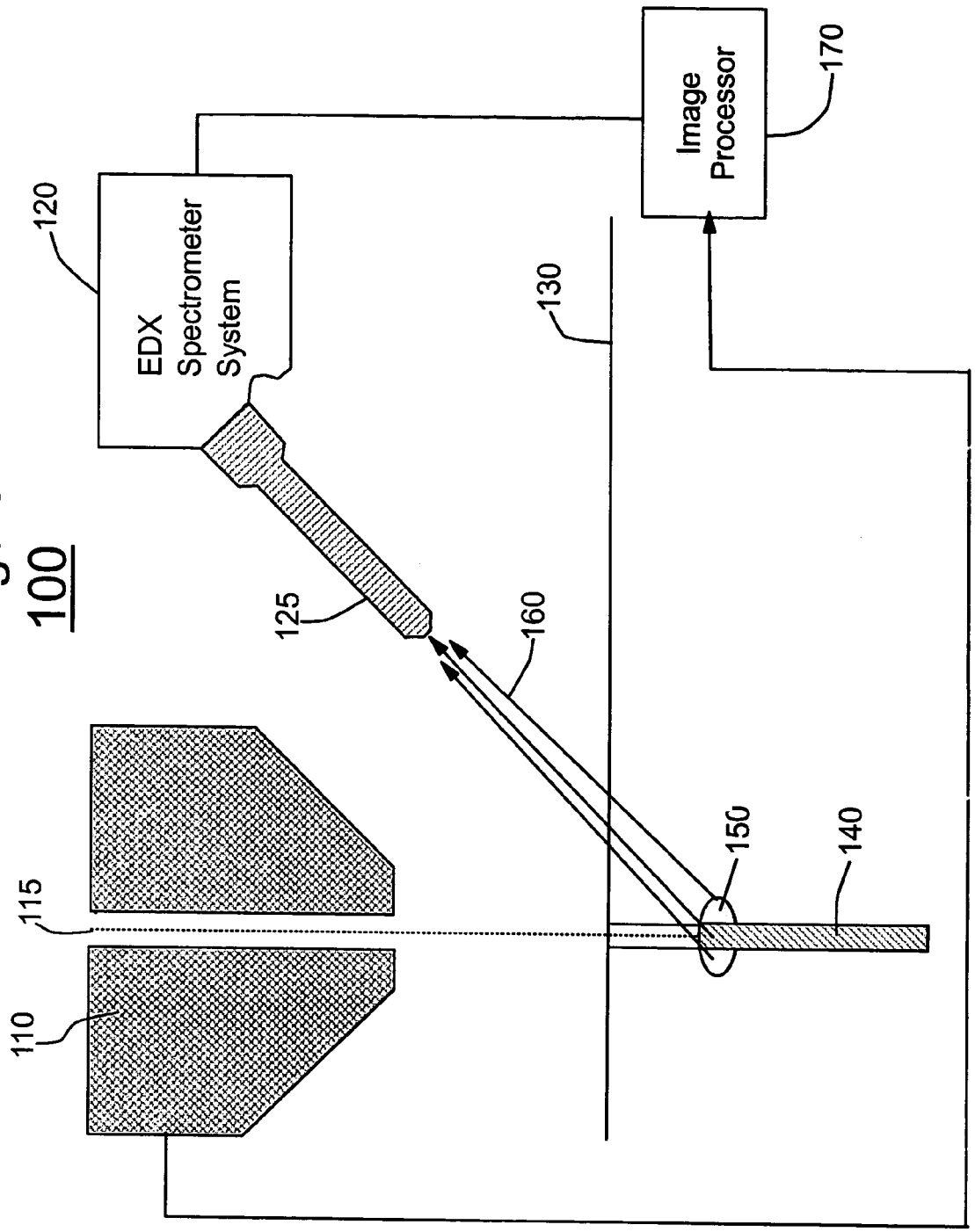
FIG. 1A illustrates a structure 100 for performing trench depth measurement according to the present invention.

Referring now to the drawings, and more particularly to FIGS. 1A–3, there are shown exemplary embodiments of the method and structures according to the present invention.

Exemplary Embodiment

Generally, to measure the depth of a trench according to the invention, a scanning electron beam is scanned over the trench, and when the beam strikes the surface of the wafer, the electrons scatter in the local area, and emit X rays. The X rays are detected by an x-ray detector. During this process, the normal SEM secondary electron detector is used simultaneously with the X-ray detector. It is customary in x ray detection to count only those x rays that fall in an energy range of interest. This is usually restricted to count only those x rays characteristic of a specific emission such as the silicon kα emission energy. These emissions are characteristic of the atomic element from which they come, and can thus be used to isolate a particular species of atom.

As the beam scans, the detector records the secondary electron counts and x ray counts in an image (i.e., keeps a record of where the beam is, and where the counts came from). The term "image" in this context is understood to mean a 2-dimensional array of counts in which the position in the array corresponds to an x, y position coordinate on the sample. Hence, as the surface of the sample is traversed with the beam, the X-ray detector makes up its own picture, and it knows where the beam was when the counts came in. The more counts there are, the brighter the image, whereas the less counts there are, the darker the image is.

As the beam scans along, if the beam is on the surface, the electrons scatter off atoms immediately adjacent to and under the impact site(s) producing characteristic x rays, and thus the X rays come from at or near Oust beneath) the surface and hence have a clear line of flight to the detector. If the electron beam is over a trench, then the electrons travel to the bottom of the trench and produce the X rays at the bottom of the trench. Hence, those X rays must travel through a large amount of material to the detector, and thus are attenuated. The x ray detector is understood to be off axis relative to the trench as shown in FIG. 1A. The normal SEM secondary electron image is collected in the usual way.

With the attenuation coefficients of the material of interest (e.g., silicon or the like) (which are well-known) and being able to calibrate the same based on a comparison with cleavage cross-sections, based on the difference in counts between the inside of the trench and the outside of the trench, the present invention can reliably estimate how much material (e.g., silicon) the X rays had to traverse through (deeper trenches result in more x ray attenuation). By knowing the angle between the wafer and the detector, the invention can triangulate and compute how deep the trench is since it is known how many microns of material the beam had to travel through to escape to the detector.

Referring now to FIG. 1A, generally, an exemplary embodiment of the method of the present invention employs a conventional scanning electron microscope (SEM) fitted with an energy-dispersive X-ray spectrometer (EDX). It is noted that a wavelength dispersive X-ray spectrometer can also be used for this application. In general, the energy dispersive method is chosen for cost and convenience.

As shown in FIG. 1A, a system 100 according to the present invention includes a scanning electron microscope (SEM) 110 fitted with an energy-dispersive x-ray spectrometer (EDX) 120.

An electron beam 115 of the SEM 110 is employed to scan the surface of a substrate (silicon wafer in this example) 130 containing a trench 140. Electrons from the SEM beam 115 impact the surface of the substrate 130 and trench 140 regions, thereby causing fluorescent and bremstralung X rays 160 to be produced at or near the point of electron impact 150.

Figure 1C:
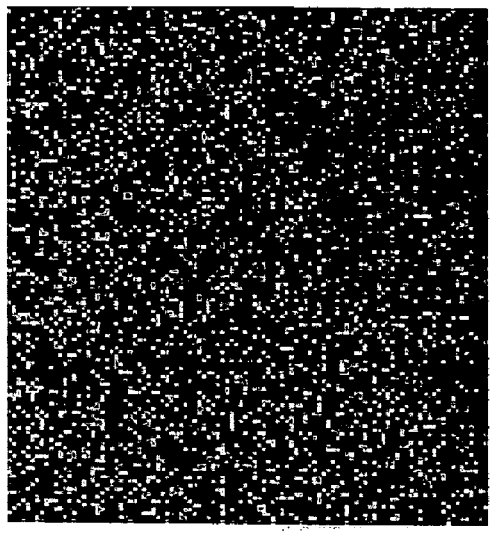
FIG. 1C illustrates a silicon X-ray image.
Figure 1B:
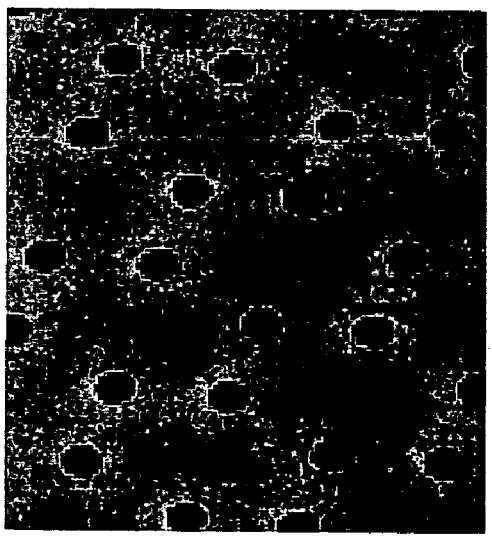
FIG. 1B illustrates an SEM secondary electron emission (SE) image.

The x-rays are detected using the EDX system 120, and an X-ray image is produced as shown in FIG. 1C. At the same time, a conventional secondary electron (SE) image is also produced by SEM 110, as shown in FIG. 1B.

The X-ray detector 125 of the EDX system 120 is preferably located at an angle relative to the electron beam, as shown in FIG. 1A. The angle of the detector is usually fixed by the design of the SEM. In the event that the angle can be adjusted, it is useful to compute it such that good contrast is achieved.

X rays emanating from the surface of the sample have a clear line of flight to the detector 125. However, X rays emanating from the base region of the trench 140 must travel through substrate 130 material to reach the detector 125, and are attenuated (shielded) by this material (e.g., silicon or the like). Thus, the X rays produced in the electron beam interaction volume are attenuated by the silicon according to depth. Hence, deeper trenches will attenuate these X rays more than shallow trenches since more material will have to be traversed by the X rays.

Hence, by comparing the number of X rays reaching the detector 125 from the surface regions of the sample 130 to the number of X rays reaching the detector 125 from the base regions of the trench 140, the depth of the trench 140 can be estimated.

To achieve an accurate practical measurement, it is necessary to count the X rays per unit area per unit time from each region (e.g., trench and surface).

One method is to generate an X-ray image that is sufficiently resolved to be able to distinguish the trench regions of the image from the surface regions. As a practical matter, this is difficult or even impossible because of the large number of counts required to achieve a well-resolved X-ray image. Charging, vibration and beam variations place a practical limit on the amount of time one can scan the sample before distortion renders the data unusable.

The present inventors have recognized that the number of counts necessary to achieve a good measurement of trench depth is significantly less than the number of counts necessary to acquire a well-resolved X-ray image. The invention takes advantage of the fact that the secondary electron image (e.g., shown in FIG. 1B) is acquired simultaneously with the X-ray image (e.g., shown in FIG. 1C).

The SE image is used to identify the regions corresponding to the surface and those corresponding to the base region of the trench 140 using histogram and image processing methods.

Once these regions have been identified, the areas corresponding to each region in the X-ray image are integrated to produce an estimate of the number of X-ray counts at a specific energy per unit area.

These two estimates are then ratioed, and compared to a calibration curve to produce an estimate of trench depth. It is understood that this can be done manually or more typically using an attached computer.

Again, it is important to note that the total number of X-ray counts required to produce an accurate depth measurement is far less than the number necessary to produce resolved X-ray image.

A typical x-ray detector will register on the order of 50,000 counts per second. Since the detector registers counts at many energies, only a fraction of this number are useful.

With recognition of this condition, the present invention typically performs its measurement by counting the X rays corresponding to the silicon K line since this is the substrate used for the trenches of interest in the exemplary DRAM manufacturing application. In cases where the base region of the trench is made of a different material, other fluorescent energies can be chosen as appropriate for the materials in question.

The accuracy of the measurement is proportional to the square root of the number of counts. Depth measurements with an accuracy on the order of a few percent require 10,000 counts or more. However, in practice, the inventors have found that a reasonable measurement can be obtained in one minute or less of scanning.

To avoid charging effects, the invention typically makes a single raster scan of the region of interest. By doing the raster scan, it is assured that points in the secondary electron image (e.g., shown in FIG. 1B) correspond exactly to the points on the X-ray image (e.g., shown in FIG. 1C). Thus, charging and raster distortions cause little ambiguity.

Returning to FIG. 1B, again a secondary electron image of an array of trench structures is shown. It is noted that the trench regions (unreferenced) are black in the image. This is due to the secondary electrons produced in the bottom of the trench having a low probability of escape, and thereby producing a low value (or dark area) in the image. The present invention takes advantage of this fact to interpret the secondary electron image.

An exemplary embodiment of the invention uses an image processor 170 to perform image processing. Image processing involves forming a histogram of the image, and tagging all points greater than a threshold value as outside (or substrate) points, and all those below the threshold as inside (or trench) points. The threshold is chosen as a fixed percentage of the range of the histogram. The invention dilates the region at the boundary between the inside and outside points to eliminate the sidewall regions of the trench from the calculation. The value of the points in the X-ray image (e.g., see FIG. 1C) corresponding to the outside and inside points are summed and normalized based on the number of pixels in each region.

It is noted that the integration time is identical for both regions. The ratio of the inside counts per unit area divided by the outside counts per unit area gives the measurement result. This result can be directly converted to a depth value using a calibration curve. FIG. 2 illustrates such a curve, and thus validates the good results of the invention.

Regarding FIG. 2, the count ratio versus depth is shown. It is noted that the count ratio is not large (e.g., in a range from about 0.6 to about 0.7), and thus not much change is occurring, and this explains why there is not a large contrast (variation) in the X-ray image.

Additionally, it is noted that since only a difference of count ratio of 0.6 to 0.7 is of interest, one should know the number accurately (e.g., preferably to about 1 percent), and thus the count time is important.

There are other effects which the present invention moderates. For example, SEMs are notorious for charging problems, etc. Hence, another advantage of the present invention is that, since imaging is being conducted over a large area, the charging problems are much less pronounced.

Thus, in contrast to a manual technique in which a beam is placed on one side and then placed in the trench/hole, one must be very careful since, if the beam is left there too long, then the area will charge up and affect the detected value. Since this is an insulating material or a semiconductor material, if a charge is pumped into the material, then a rapid space charge will be built up in the area, thereby rejecting further electron penetration. Hence, there is a limited amount of time in which to count. By distributing the beam over a larger area, it becomes much less of a problem.

It is noted that the above range (e.g., 0.6 to about 0.7) is exemplary only, and depends upon a variety of factors including an amount of attenuation properties of the material (e.g., the depth of the trench, the type of material, etc.) and the distance traveled. Hence, again, FIG. 2 represents, in a case of practical interest, that the invention achieves numbers which are consistent with controlling the process. The choice of e-beam energy, x ray detector region of interest, etc. must be chosen in a manner appropriate for the structure being examined. For example, deeper trenches may require higher beam energy and a different substrate material would require the choice of an x ray detector energy region of interest corresponding to characteristic emission energies of that material.

In sum, in one practical application, the invention measures the depth of deep trenches in a material (e.g., an array formed of silicon having a plurality of trench memory or MEMs devices).

It is noted that the basic method of measuring the x ray counts inside the trench feature relative to those outside the feature can be performed manually or automatically on single isolated features by placing the beam in the feature, counting the x rays, then placing the beam outside the feature and counting the x rays, computing the count ratio and finally computing the feature depth using the calibration curve. The image-based methods described above are used for convenience to address the far more common case where arrays of identical features are to be measured.

To make the measurement, the invention uses an SEM which makes an image (e.g., a secondary electron image). At the same time, the X-ray system is also making an image, but this image has far fewer counts in it. The invention recognizes that the SEM image is a high quality image (relatively) and if one uses the SEM image to navigates, one can determine where all of the holes are and where all of the surface spots are.

Additionally, since all of the holes are nominally of the same approximate depth (in most practical cases), then it makes no difference if the count comes from a first hole, an intermediate hole, or a final hole. All that is important is that the total number of counts is large enough that an accurate estimate of the depth of all of the holes can be obtained. It is a characteristic of the etch processes used in semiconductor processing that the trenches in a local area are etched to the same depth to high precision.

Thus, the invention separates the counts in the x-ray image, using the SEM image, into inside and outside counts, by simply going through the SEM image and image processing it to find the holes (trenches), and then going to those regions in the x-ray image corresponding to those holes and counting the counts in those areas, and then ratioing them to the counts in all of the other areas. Using this method, one can estimate the count ratio, and, from that ratio, the depth of the trench.

Again, the invention knows in advance that it is dealing with many trenches formed in an array, all having the same depth, and thus one need not exhaustively count for a very long time, but instead one can get information on all of them simultaneously, and get the answer/estimate relatively quickly because 10,000 counts can be obtained rather quickly to make the estimate (e.g., a reasonably accurate estimate since 10,000 counts have been obtained).

Again, an important aspect of the invention is using the SEM image to navigate to the trenches/holes in the X-ray image.

That is, the SEM image has a one-to-one correspondence to the X-ray image, and allows one to correspond the image in the SEM to the X-ray image. Hence, whereas the x-ray image (e.g., FIG. 1C) is not clear and does not show enough dots (counts) to show the form and outline of the trenches/holes, the SEM image is clear and crisp. Thus, the SEM image can inform the user where the holes/trenches are much quicker than the X-ray image will.

However, so long as the total number of counts inside the holes/trenches in the X-ray image, it does not matter if the features can be seen in the X-ray image. Indeed, normally they cannot be seen in the X-ray image. However, while there is typically not enough contrast in the X-ray image to provide the visual acuity enough to pick out one point from another, there is enough contrast in the SEM image. Thus, the SEM image allows navigating to the features in the X-ray image (and thus the depth information).

In practice, the inventive method is effective on trenches in the 1–3 micron depth range in silicon, but the benefit of the invention may be higher the deeper the trench becomes (e.g., because measuring with a probe becomes more difficult the deeper the trench is). Hence, the invention may be operable for trenches having a depth up to about 100 microns or more. More specifically, the invention is especially good for high aspect ratios (e.g., on the order of about 10:1 and less than several hundred nanometers) where a probe, such as an AFM, cannot go (or it is difficult to go).

The benefit of the invention may not be as keenly felt in shallow trenches (e.g., such as those less than about 0.5 microns deep) unless the material (e.g., such as gold) is very heavily attenuated to X rays and has high stopping power for electrons.

Thus, for example, if the invention was trying to measure trenches in a conductor (e.g., copper), the penetration depth of copper is very low and the stopping power of X rays in copper is very high. Therefore, the contrast would be very high, and thus going to very shallow trenches (e.g., less than about 0.1 micron deep) would still provide meaningful results.

Turning to FIG. 3, a flowchart is provided of the inventive method 300 of non-destructive measurement of a depth of a feature in a structure.

In step 310, a scanning electron microscope (SEM) image is used to navigate to find the feature in an X-ray image.

In step 320, an electron beam is used to produce fluorescent emissions in the feature.

Then, in step 330, an X-ray count, made at inside and outside positions of the feature in the x-ray image, is used to determine a depth of the feature.

While the invention has been described in terms of several exemplary embodiments, those skilled in the art will recognize that the invention can be practiced with modification within the spirit and scope of the appended claims.

For example, a scanning beam is used advantageously by the invention. Instead of the SEM discussed above, a scanning focused ion beam (FIB) could be employed for providing a scanning beam (e.g., atoms such as gallium, etc.), thereby to provide the X-ray production.

Thus, for example, an ion beam could be employed which interacted with the sample to cause a detectable particle emission (e.g., either radiative or particulate), and the above-described principles of the invention would equally apply. Thus, for example, if a proton beam was being scanned and looking for some nuclear reaction as evidenced by some particles coming out of it, the invention's principles would apply. Hence, looking at Beryllium with an alpha beam, when an alpha beam strikes Beryllium, it gives off neutrons which can be counted (e.g., with a neutron detector). Thus, given a neutron detector and an alpha particle beam, results can be obtained similar to those described above with regard to the embodiment of FIG. 1A.

Hence, the invention can be generalized to a scanning beam of either photons or particles, resulting in collision and emission of either photons or particulate energy which can be detected elsewhere, and is attenuated by the subject material.

The invention also is not limited necessarily to the X-ray detector. The geometry of the material attenuates enough radiation coming from the impact point such that some form of radiation gets out (escapes), so that it can be detected, and thereby to provide a measurement.

Further, it is noted that, Applicant's intent is to encompass equivalents of all claim elements, even if amended later during prosecution.

What is claimed is:

1. A method of non-destructive measurement of a depth of a feature in a structure, comprising:

navigating and locating said feature using a scanning electron microscope (SEM) image;

producing fluorescent emissions in said feature using the electron beam from said SEM;
producing fluorescent emissions outside said feature using the electron beam from said SEM;
counting, using an X-ray detector and a counting apparatus, said fluorescent emissions located such that emissions outside said feature travel through less structure than those inside said feature; and
determining a depth of said feature based on a count of said fluorescent emissions made at inside and outside positions of said feature.

2. The method of claim 1, wherein said feature comprises a trench formed in said structure, said structure comprising a semiconductor substrate.

3. The method of claim 1, further comprising:
scanning the electron beam over said structure, and such that when the beam hits a surface of the structure, electrons scatter in a local area, and emit X rays; and
detecting said X rays.

4. The method of claim 3, further comprising:
as the beam scans, judging a position of said beam and determining a position from where counts of said X rays originated.

5. The method of claim 4, further comprising:
as the structure is traversed with the beam, forming a record of X-ray counts versus position in at least one dimension.

6. The method of claim 3, further comprising:
based on a difference in counts between an inside position of the feature and an outside position of the feature, estimating an amount of material of said structure the X rays passed through.

7. The method of claim 1, wherein said X-ray detector forms an X-ray image, said method further comprising:
based on an angle between the structure and the X-ray detector, triangulating and computing said depth of the feature.

8. An apparatus for non-destructive measurement of a depth of a feature in a structure, comprising:
a scanning electron microscope (SEM) for producing an image for navigating to find said feature in an X-ray image; and
means for using an X-ray count made at a position of said feature in said X-ray image, to determine a depth of said feature.

9. A system for non-destructive measurement of a depth of a feature in a structure, comprising:
a scanning electron microscope (SEM) for scanning an electron beam across a surface of a substrate containing a feature; and
an X-ray detector for detecting X rays produced when said electron beam strikes the surface of the substrate, and producing an X-ray image,
wherein electrons from the electron beam impact the surface of the substrate and feature regions, thereby causing X rays to be produced adjacent a point of electron impact, said SEM forming an SEM image.

10. The system of claim 9, wherein the electron beam produces a fluorescent emission in said feature, said system further comprising:
a processor for using a count of said emission made at a position of said feature in said X-ray image, to determine a depth of said feature.

11. The system of claim 10, wherein the X-ray detector is located at an angle relative to the electron beam, such that X rays emanating from the surface of the substrate have a clear line of flight to the detector, and wherein x-rays emanating from a base region of the feature travel through said substrate to reach the detector, and thereby to be attenuated by said substrate.

12. The system of claim 11, wherein the X rays produced in the electron beam interaction volume are attenuated by the substrate according to depth.

13. The system of claim 9, further comprising:
an image processor for processing the image, said processor comparing a number of X rays reaching the detector from the surface regions of the substrate to a number of X rays reaching the detector from base regions of the feature, and for estimating the depth of the feature.

14. The system of claim 9, wherein the X-ray detector counts the X rays per unit area per unit time from the feature regions and the surface region.

15. The system of claim 9, wherein a secondary electron image is acquired simultaneously with the X-ray image.

16. The system of claim 9, wherein a secondary electron image is used to identify surface regions corresponding to the surface and base regions corresponding to a base of the feature.

17. The system of claim 16, further comprising:
an image processor for processing said X-ray image,
wherein after identifying the surface and base regions, areas corresponding to each region in the X-ray image are integrated by said image processor to produce an estimate of a number of X-ray counts at a specific energy per unit area.

18. The system of claim 17, wherein said image processor ratios the estimates, and compares the estimates to a calibration curve to produce an estimate of the depth of the feature.

19. The system of claim 9, wherein points in a secondary electron image produced by the SEM correspond substantially exactly to points on the X-ray image.

20. The system of claim 9, further comprising:
an image processor for processing said X-ray image,
wherein said image processor forms a histogram of the image, and said image processor identifies points greater than or equal to a threshold value as substrate points, and identifies points below the threshold as feature points,
wherein the threshold is chosen as a fixed percentage of a range of the histogram.

21. The system of claim 20, wherein said image processor sums a value of the points in the x-ray image corresponding to the substrate, and normalizes the summed value based on a number of pixels in each region, and
wherein said image processors provides a measurement result based on a ratio of the feature counts per unit area divided by the surface counts per unit area, and
wherein the measurement result is converted to a depth value using a calibration curve.

22. The system of claim 9, wherein said X-ray detector comprises an energy dispersive X-ray spectrometer.

23. The system of claim 9, wherein said X-ray detector comprises a wavelength dispersive X-ray spectrometer.

24. A method of measuring a depth of a trench in a material, comprising:
scanning a surface to form a secondary electron emission (SE) image and simultaneously forming an X-ray image with an X-ray system, said X-ray image having fewer counts than said secondary electron image; and
using the SE image to determine a location of the trench in said material and a location of a surface of said material.

25. The method of claim 24, wherein a plurality of trenches are provided each having a same approximate depth, said method further comprising:

taking counts from any of said plurality of trenches, wherein a total number of counts has a predetermined size such that an estimate of the depth of all of the trenches is obtainable;

separating the counts in the X-ray image, using the SE image, into inside and outside counts, by processing the SE image to judge the trenches, identifying regions in the X-ray image corresponding to the trenches and counting the counts in said regions;

ratioing the counts to the counts in all of the other areas, to estimate the count ratio, and, from the count ratio, the depth of the trench.

26. The method of claim 24, wherein the SE image has substantially a one-to-one correspondence to the X-ray image, such that the SE image identifies where the trenches are in the X-ray image.

27. The method of claim 24, wherein the trenches have a depth within a range of about 1 to about 100 microns.

28. A method of measuring a depth of a trench in a material, comprising:

traversing a scanning beam across a surface having a trench, said scanning beam interacting with the sample to cause a detectable particle emission; and counting said detectable particle emission, to judge the depth of the trench.

29. The method of claim 28, wherein said particle emission comprises one of a radiative emission and a particulate emission.

30. The method of claim 28, wherein said emission comprises any of X rays and neutrons.

31. The method of claim 28, wherein said scanning beam comprises any of a secondary electron beam and an alpha particle beam.

32. A method, comprising:

traversing a sample with a scanning beam of one of photons and particles, resulting in collision and emission of one of photon and particulate energy; and detecting the emission, attenuated by a material of the sample, to measure a dimension of a feature in said sample.

33. A method of non-destructive measurement of a depth of a feature in a structure, comprising:

using a scanning electron microscope (SEM) image to navigate to find the feature in an X-ray image;

using an electron beam to produce a fluorescent emission in the feature; and using a count of x ray emission made at a position of the feature in the X-ray image and adjacent areas, to determine a depth of the feature.

* * * * *